United States Patent
Kusenko

(10) Patent No.: US 7,291,162 B1
(45) Date of Patent: Nov. 6, 2007

(54) BODY JUMPERS TO RESTORE ENERGY FLOW IN A HUMAN BODY TO ITS NATURAL PATHWAY

(76) Inventor: Michael A. Kusenko, RR 1 Box 245D, Sigel, PA (US) 15860

( * ) Notice: Subject to any disclaimer, the term of this patent is extended or adjusted under 35 U.S.C. 154(b) by 505 days.

(21) Appl. No.: 10/605,404

(22) Filed: Sep. 29, 2003

(51) Int. Cl.
*A61N 1/00* (2006.01)

(52) U.S. Cl. .......................................... 607/1

(58) Field of Classification Search ............... 600/372, 600/382, 393; 607/2, 115, 152, 1; 601/15; 2/902
See application file for complete search history.

(56) References Cited

U.S. PATENT DOCUMENTS

| | | | |
|---|---|---|---|
| 4,580,572 A * | 4/1986 | Granek et al. ............. 600/388 |
| 5,643,329 A * | 7/1997 | Solomonow et al. ......... 607/43 |
| 6,132,452 A * | 10/2000 | Pinter ............................ 607/1 |
| 6,178,357 B1 * | 1/2001 | Gliner et al. ............... 607/142 |
| 6,277,142 B1 * | 8/2001 | Pinter ............................ 607/1 |
| 2004/0044384 A1 * | 3/2004 | Leber et al. .................. 607/88 |
| 2004/0176806 A1 * | 9/2004 | Markoll ......................... 607/2 |

* cited by examiner

*Primary Examiner*—George R. Evanisko
(74) *Attorney, Agent, or Firm*—John J. Elnitski, Jr.

(57) ABSTRACT

A method of restoring energy in the human body to its natural pathway using body jumpers. The body jumpers are either a set of two or three electrical conducting pads which are interconnected. The method involves proper placement of the body jumpers on a human body and holding the body jumpers in place for a certain amount of time. The method and set of body jumpers employed depends on the results of a muscle test.

6 Claims, 8 Drawing Sheets

BODY JUMPERS TO RESTORE ENERGY FLOW IN A HUMAN BODY TO ITS NATURAL PATHWAY

BACKGROUND OF INVENTION

The present invention generally relates to the healing of alignments of the human body. More specifically, the present invention relates to manipulation of energy pathways in the human body.

The energy pathways of the human body are referred to as meridians. The energy pathways become congested from the daily living and the consumption of the many pathogens and chemicals that ingested by the human body. Current day to day living appears to be some of the most congesting to the energy pathways that humanity may have ever experienced. The mere act of living today causes the disruption of these pathways leading to sickness both physically and mentally. The stagnation of the human body energies are leading to more auto-immune diseases in younger and younger people.

When the energy can not flow like it should, congestion starts and the coagulation of these energies produce a thickening of the mucous in various parts of the human body. This thickening starts in the muscles and if not relieved will progress to various glands and organs making it difficult for the energies to flow through their normal pathways. When the energies can not take their normal pathway, they seek another route or outlet for their continuing pulsations. When the energies start to move in a direction that is not normal, the human body starts to run down and nothing works like it should. This is referred to as a switching or in kinesiology terms, the human body polarity is said to be reversed. When this happens, what was good for the human body before is now bad for the human body. In kinesiology, when the human body polarity is reversed, the testing will not work or the responses will be erratic. Most of the systems of the human body will now test weak. This weakness will show up as a lack of strength during muscle testing and will also show up as a weakness in the human body, such as labored breathing when walking a very short distance. Digestion will become sluggish along with the assimilations and eliminations. The human body metabolic rate will continue to become slower which will result in the human body becoming larger and over time completely worn out. When the energy can not flow properly, the natural course of flow will build up and sometimes cause a shaking of the human body or create tremors in various body parts or over the entire human body. This switching sometimes causes vertigo or the feeling of unstableness and actually falling down. This condition causes the brain to not function properly, thereby creating confusion, causing the inability to think, causing the inability to put thoughts together, causing memory loss and many other conditions.

It is an object of the present invention to provide an apparatus and method of use of such apparatus to manipulate the human body energies along the proper pathways when the human body energies travel improper pathways.

SUMMARY OF INVENTION

A method of restoring energy in the human body to its natural pathway using body jumpers. The body jumpers are either a set of two or three electrical conducting pads which are interconnected. The method involves proper placement of the body jumpers on a human body and holding the body jumpers in place for a certain amount of time. The method and set of body jumpers employed depends on the results of a muscle test.

DETAILED DESCRIPTION

Figure 1:
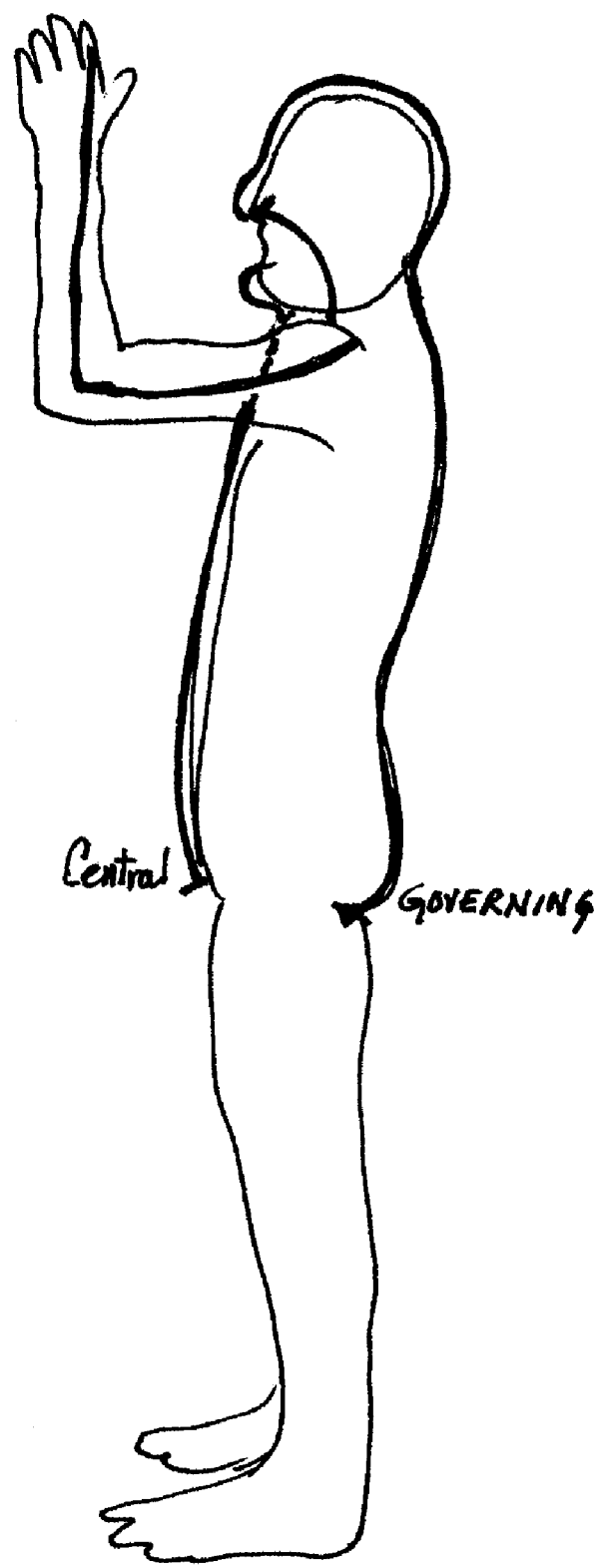
FIG. 1 is a schematic view of the central and governing meridians in the body according to the present invention.
Figure 3:
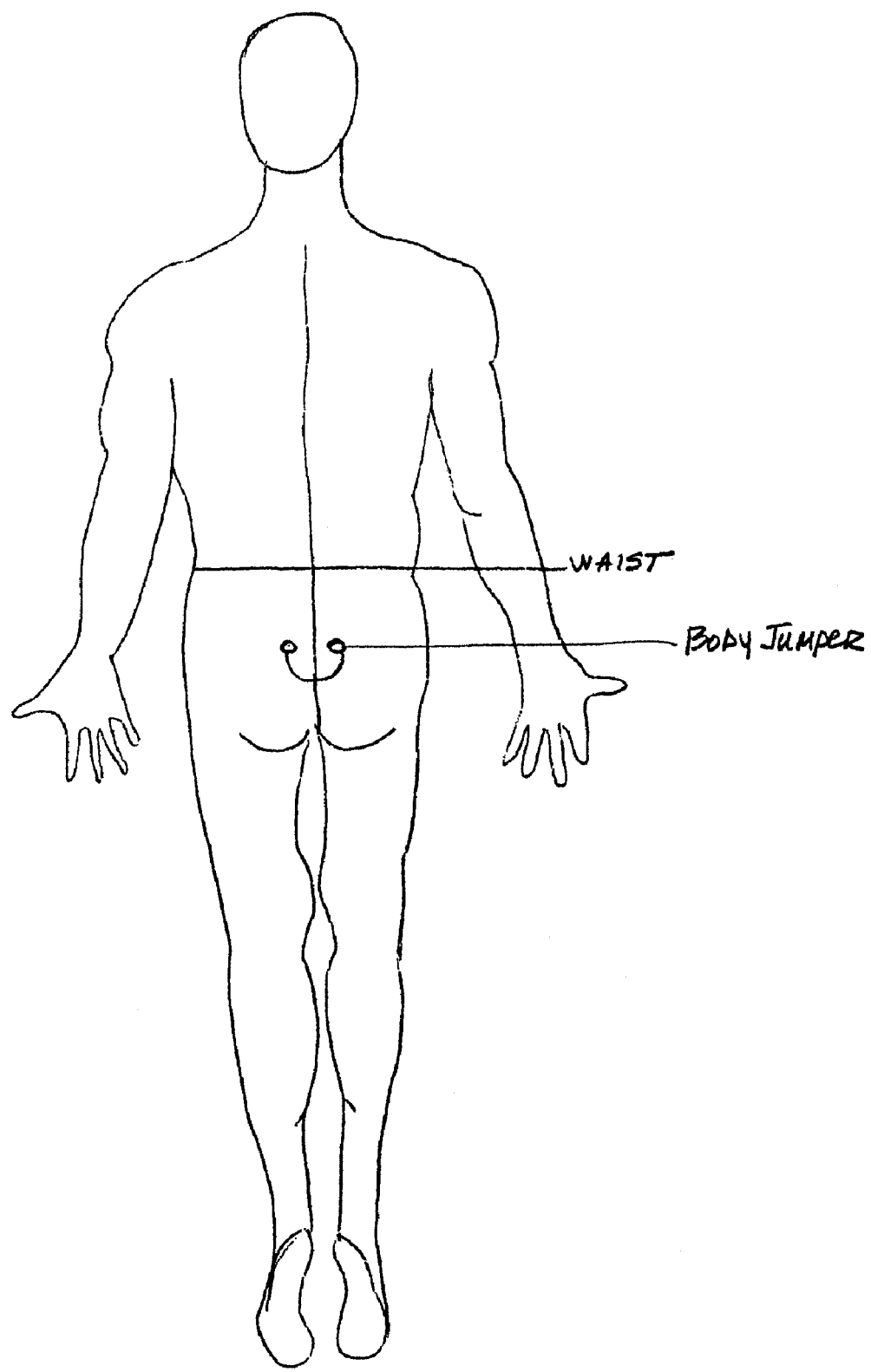
FIG. 3 is a schematic view of placement of the 2-point jumper configuration for the governing meridian according to the present invention.
Figure 4:
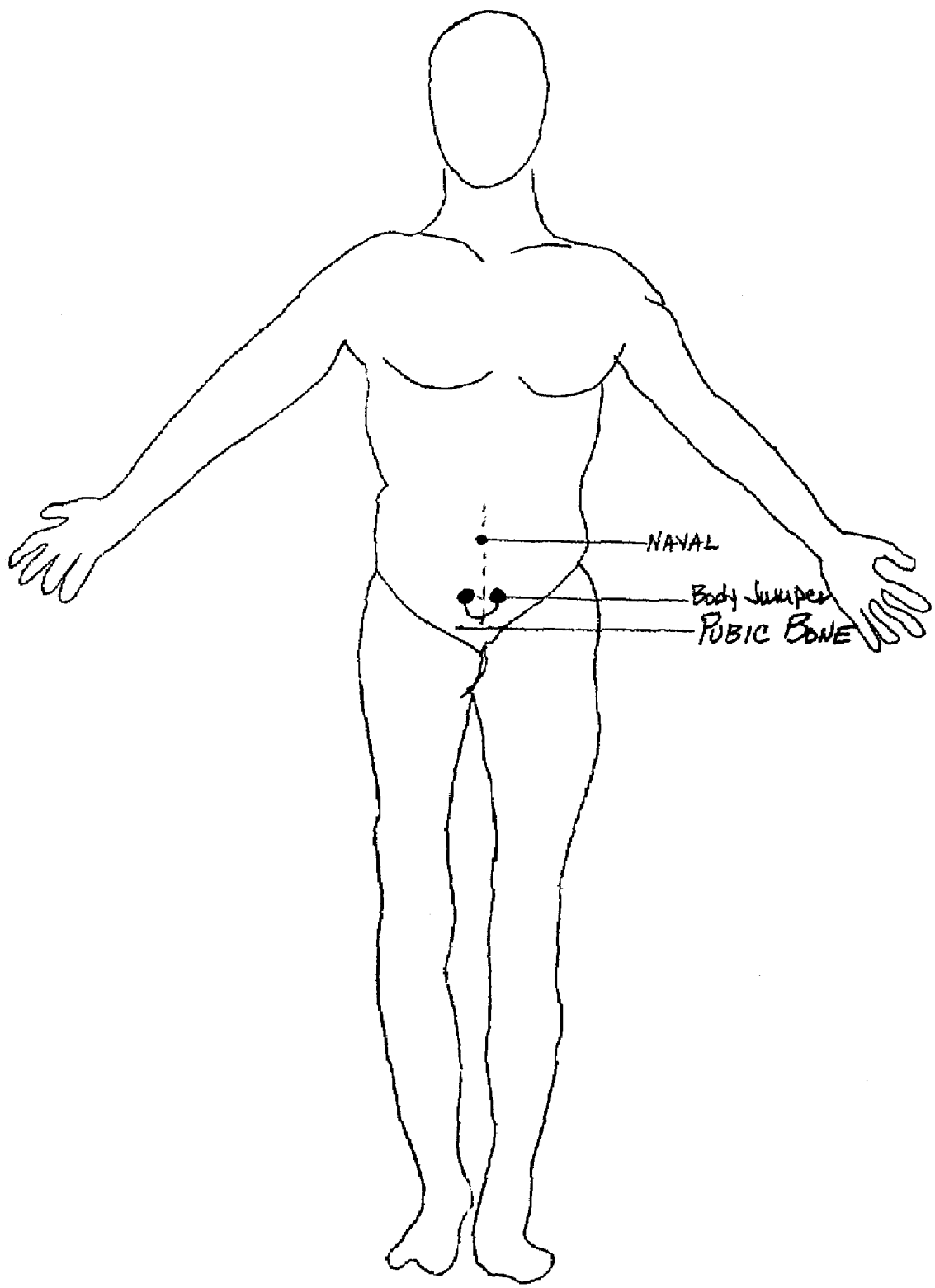
FIG. 4 is a schematic view of placement of the 2-point jumper configuration for the central meridian according to the present invention.
Figure 5:
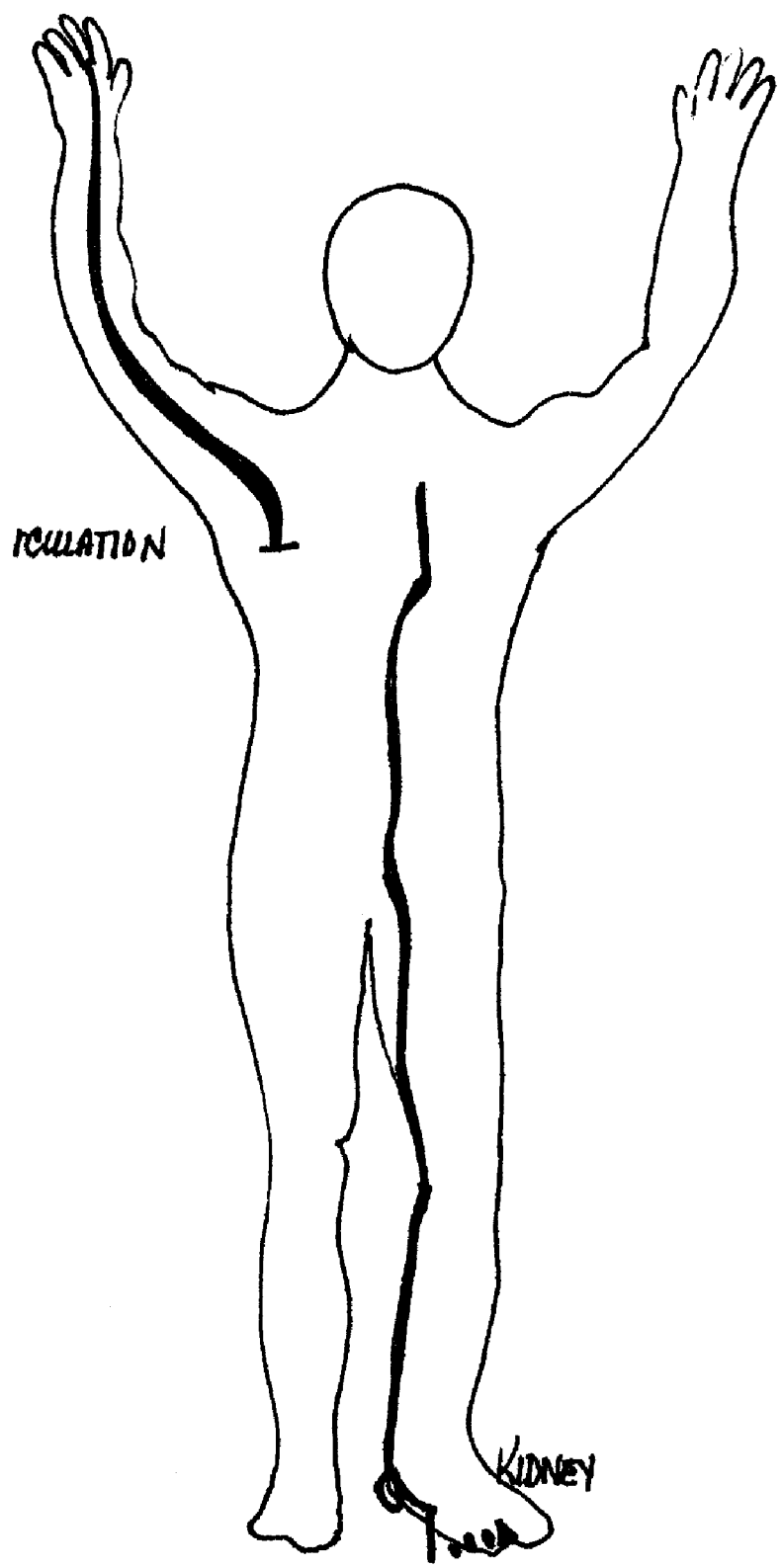
FIG. 5 is a schematic view of the meridians for the kidney and circulation in the body according to the present invention.
Figure 6:
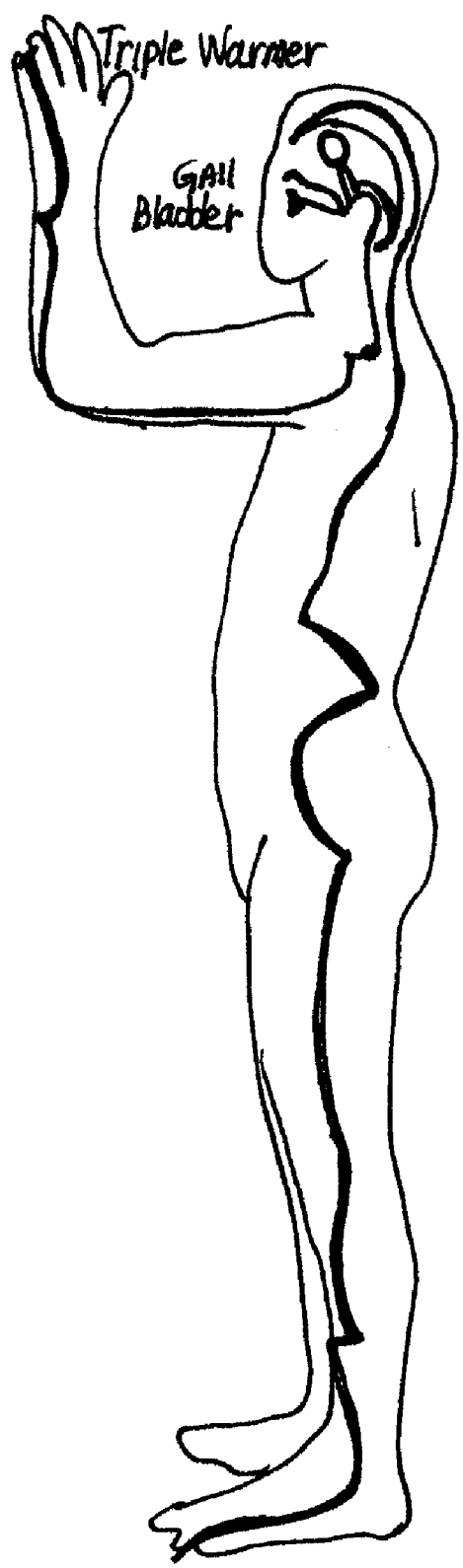
FIG. 6 is a schematic view of the meridians for the gall bladder and triple warmer in the body according to the present invention.
Figure 7:
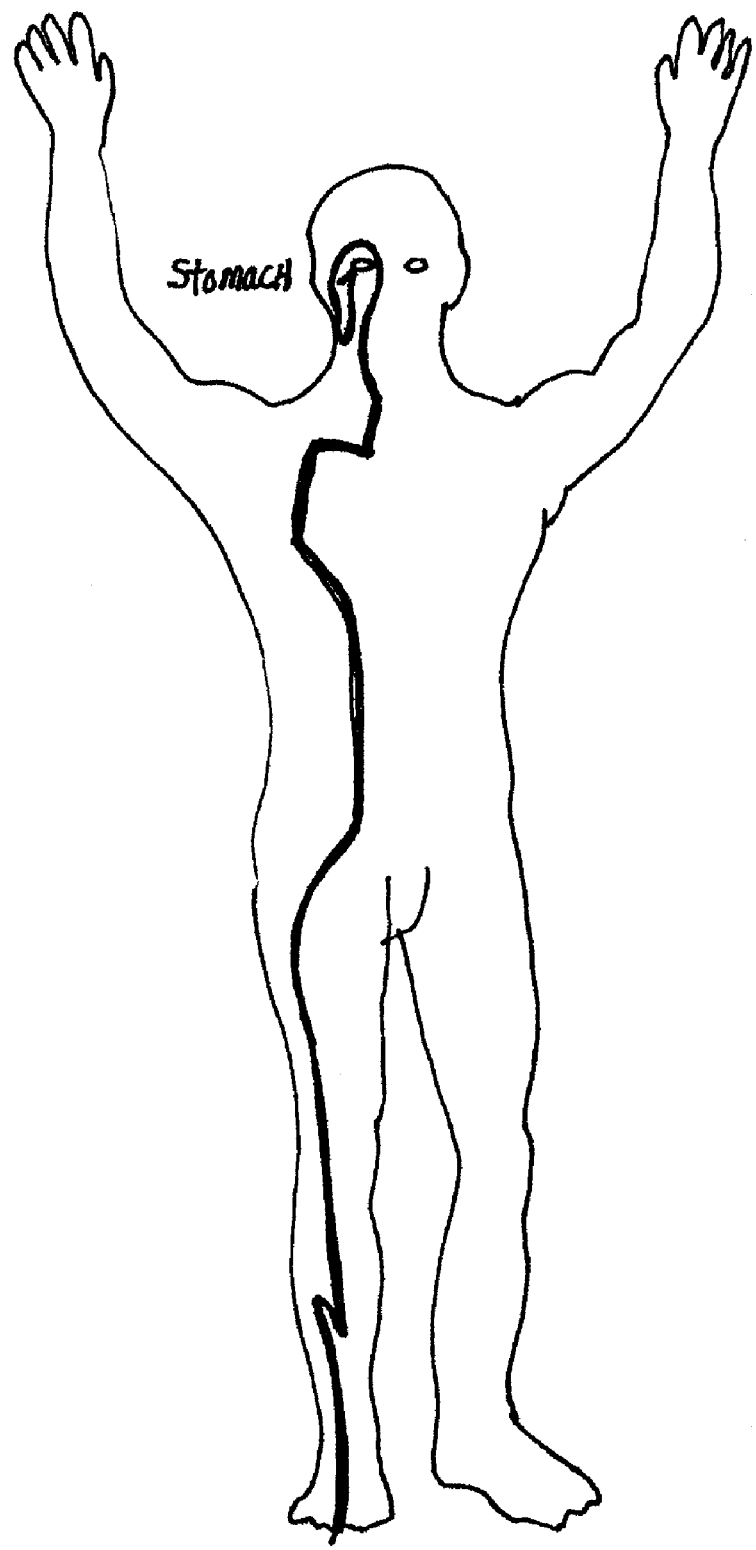
FIG. 7 is a schematic view of the meridian for the stomach in the body according to the present invention.
Figure 8:
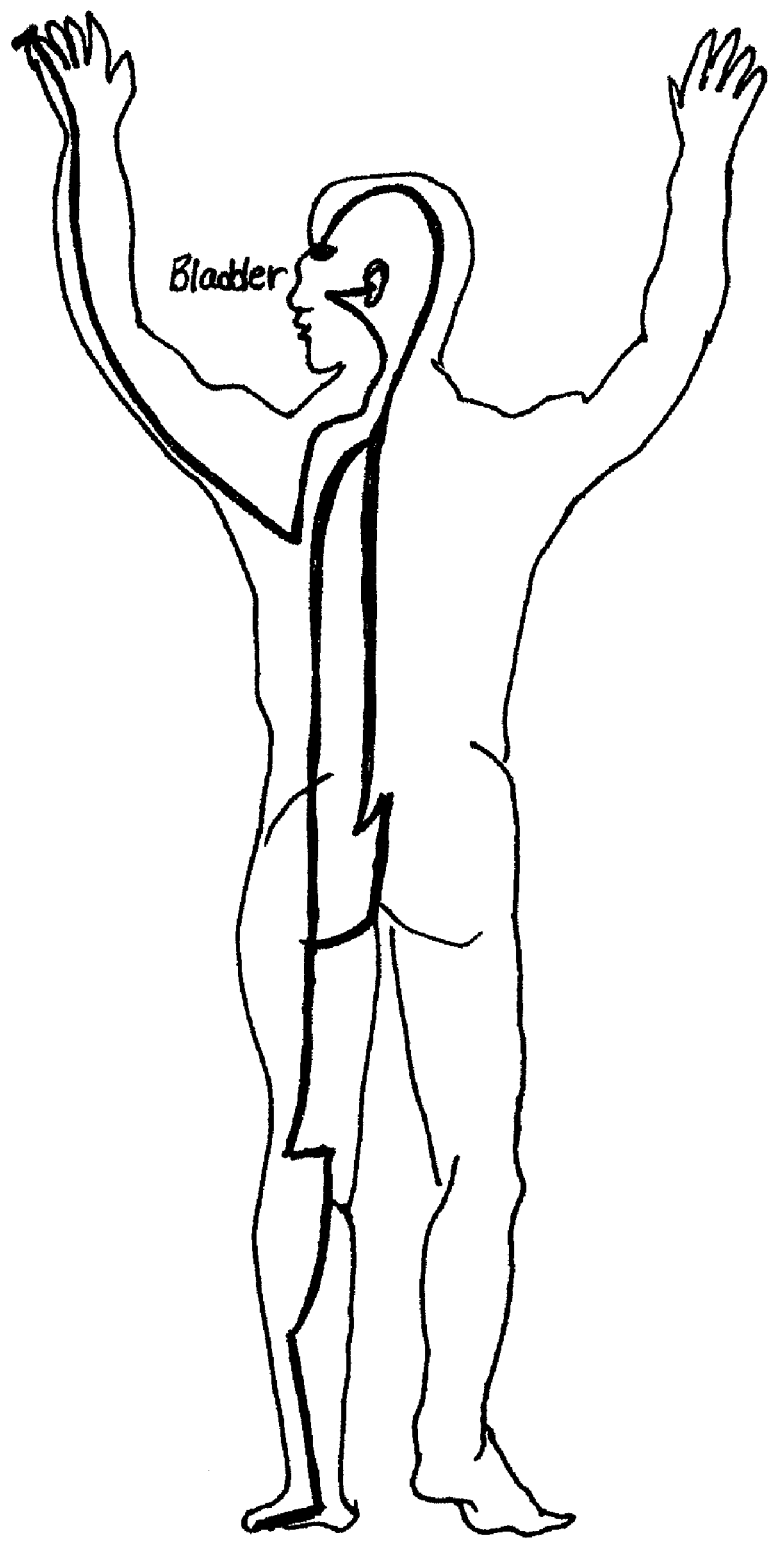
FIG. 8 is a schematic view of the meridian for the bladder in the body according to the present invention.

The present invention is a series of body jumpers and the method of use of the body jumpers. FIG. 1 shows the central and governing meridians of the human body. The central meridian starts at the pubic bone and goes up the front of the body to the lower lip. The governing meridian starts at the tail bone and goes up over the head and ends at the upper lip. By working with the central and governing meridians and by proper placement of the body jumpers, the energy can be restored to its natural pathway. The body jumpers are metallic pads with conduct electrical current. There are two configurations of the body jumpers. The first is a 3-point jumper configuration and the second is a 2-point jumper configuration. The 3-point jumper is three pads interconnected by two electrical current conduction wires, as show in FIG. 2. The 2-point jumper is two pads interconnected by one electrical current conduction wire, as show in FIGS. 3-4.

There is a simple muscle test to determine if the polarity of the body is switched. This test is performed in three separate ways to determine where to place the body jumpers and which configuration to use. The muscle test steps are as follows. Place the thumb and middle finger of the right hand together at the tips, so that the tips touch and the thumb and middle finger of the right hand make a circle. Take the thumb and index finger of the left hand and put the thumb and index finger so that the first phalanges of the thumb and index finger are parallel. Insert the thumb and index finger of the left hand through the circle formed by the right hand. Instruct the brain mentally to keep the thumb and finger together for a "Yes" and to open for a "No" answer. With the finger and thumb of the left hand inserted through the circle made by the right hand, try to open the fingers of the left hand, while mentally questioning is the polarity of the body switched. If resistance is met from the fingers of the right hand while trying to open the fingers, the answer is "Yes". When the same question is asked and there is a weakness in the right hand and the fingers respond by opening, the answer is "No".

Figure 2:
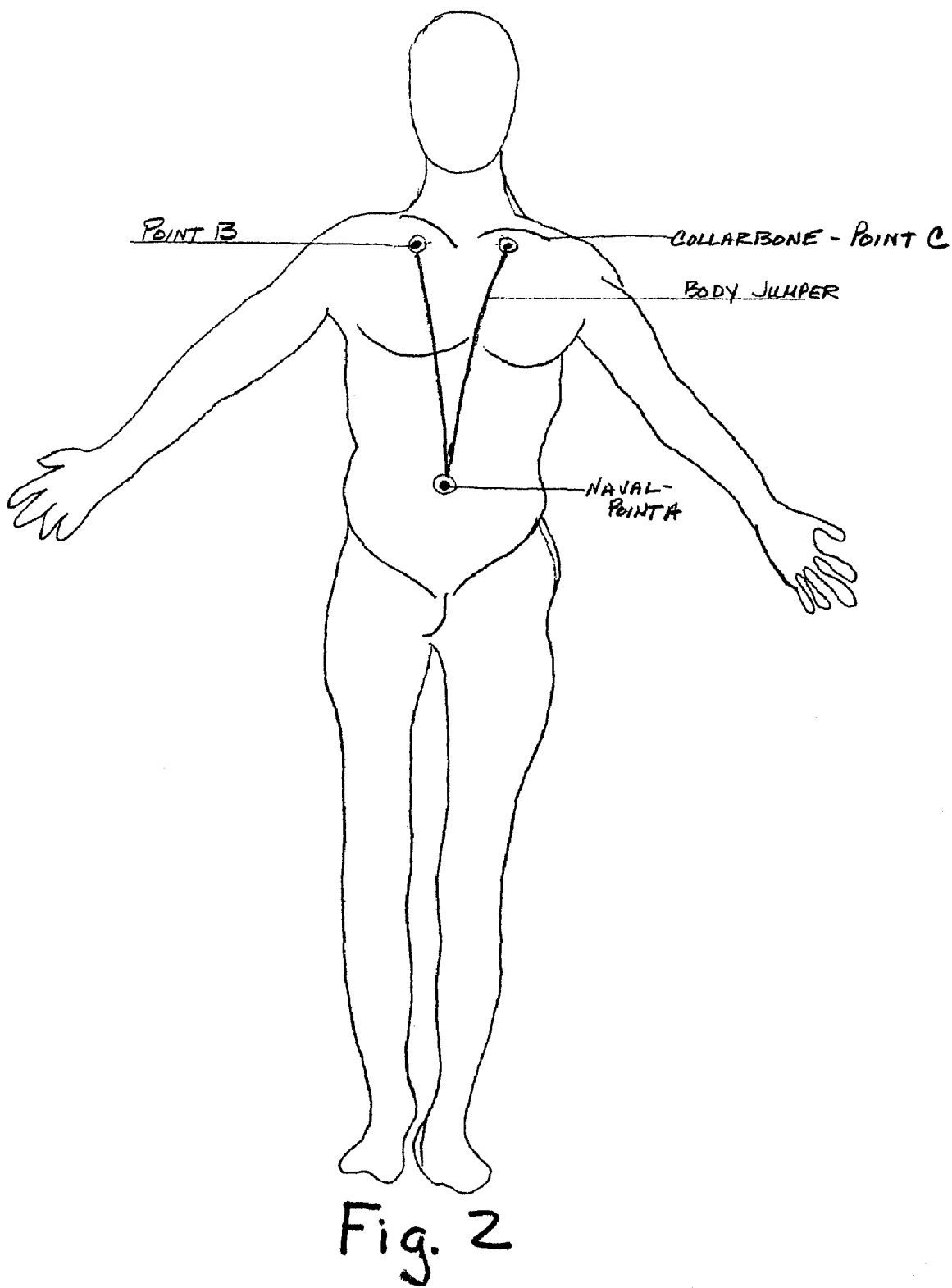
FIG. 2 is a schematic view of placement of the 3-point jumper configuration according to the present invention.

If the muscle test of the body's polarity is performed and the polarity is switched, the 3-point jumpers are used, as shown in FIG. 2. The first pad is placed at point A over the belly button. The second pad is placed at point B on the left side of the body below the collar bone in the natural depression that is about mid-point between the shoulder and center line of the body. The third pad is placed at point C on the opposite side in the same area as the second pad. This position of the first, second and third pads should be held for two to three minutes.

By crossing the feet at the ankles and performing the muscle test, it can determine if the body is switching in the central meridian or the governing meridian. When the ankles are crossed over right over left and it is determine that the body is switched by the muscle test, the governing meridian is switched. To switch back to normal, the 2-point jumpers are used. The body has two indentations on the back, one on either side of the spine, about midway between the tailbone and the waist. Place the two pads, one on either side of the spine in these indentations and hold this position for one to two to three minutes and polarity will be switched back to normal for the governing meridian. When the ankles are crossed over left over right and it is determine that the body is switched by the muscle test, the central meridian is switched. To switch back to normal, the 2-point jumpers are used. Place the two pads about one inch above the pubic bone, one on either side of the front of the body about three inches apart. Hold this position for to three minutes and polarity will be switched back to normal for the central meridian. All three of these methods switch the polarity back to its normal course and the energy will start flowing normally.

There are numerous ways to place the body jumpers to transfer the energy from one point to another in the body and cause the points that are being held to cleanse the various organs or systems of the body and in some cases will relieve pain. FIGS. 5-8 show meridians for the stomach, bladder, circulation, kidney, triple warmer and the gall bladder. When using the 3-point jumpers as in FIG. 1, central meridian is connected with the stomach and the kidney meridians and boosting the energy in the meridian that is weak. When using the 2-point jumpers on the central meridian, you are jumping the stomach and the kidney across the central between the belly button and the pubic bone. When using the 2-point jumpers on the governing meridian, you are crossing the bladder meridian and the triple warmer meridian. The reason the body jumpers work along with the method is that the body always has energy in various segments and systems. Sometimes the energy in one system or meridian gets low and causes the body to not function like it should in one or more segments of its systems. Use of the body jumpers allows access one system that has energy to supply or transfer some of that energy to another system that has low energy, such that the body starts to go into homeostasis. There are times when all that is needed to start homeostasis is a little more energy to help the body acquire this state.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

The invention claimed is:

1. A method of restoring internal energy flow in the human body of a patient to a natural pathway of the body, consisting of:

placing a first pad with one electrical conductor in direct contact with the patient over the belly button of the body;

placing a second pad with one electrical conductor in direct contact with the patient at point on the left side of the body below the collar bone in a natural depression that is about mid-point between a left shoulder and center line of the body;

placing a third pad with one electrical conductor in direct contact with the patient at point on the right side of the body below the collar bone in a natural depression that is about mid-point between a right shoulder and center line of the body;

providing an electrical connection between the first pad and the second pad by having an electrical conducting wire between the first pad and the second pad;

providing an electrical connection between the first pad and the third pad by having an electrical conducting wire between the first pad and the third pad; and holding the position of the first, second and third pads for about two to three minutes to allow the transfer of the internal energy flow in the body to its natural pathway.

2. A method of restoring internal energy flow in the human body of a patient to a natural pathway of the body, comprising:

performing a muscle test to determine if polarity of the body is switched, the muscle test comprising:

placing a thumb and middle finger of a right hand together at tips of the thumb and middle finger of the right hand, so that the tips touch and the thumb and middle finger of the right hand make a circle;

taking a thumb and index finger of a left hand and positioning the thumb and index finger of the left hand so that first phalanges of the thumb and index finger of the left hand are parallel;

inserting the thumb and index finger of the left hand through the circle formed by the right hand;

mentally instructing a brain of the body to keep the thumb and finger of the right hand together for a Yes and to open for a No answer;

with the finger and thumb of the left hand inserted through the circle made by the right hand, trying to open the fingers of the left hand while questioning is the polarity of the body switched, if resistance is met from the fingers of the right hand while trying to open the fingers of the right hand, the answer is Yes, the polarity is switched, if there is a weakness in the right hand and the fingers respond by opening, the answer is No, the polarity is not switched; and restoring internal energy flow in the human body of a patient to the natural pathway of the body for the polarity being switched, comprising:

placing a first pad with one electrical conductor in direct contact with the patient over the belly button of the body;

placing a second pad with one electrical conductor in direct contact with the patient at point on the left side of the body below the collar bone in a natural depression that is about mid-point between a left shoulder and center line of the body;

placing a third pad with one electrical conductor in direct contact with the patient at point on the right side of the body below the collar bone in a natural depression that is about mid-point between a right shoulder and center line of the body;

providing an electrical connection between the first pad and the second pad by having an electrical conducting wire between the first pad and the second pad;

providing an electrical connection between the first pad and the third pad by having an electrical conducting wire between the first pad and the third pad; and holding the position of the first, second and third pads for about two to three minutes to allow the transfer of the internal energy flow in the body to its natural pathway.

3. A method of restoring internal energy flow of a patient along a governing meridian in the human body to a natural pathway of the body, consisting of:

placing a first pad with one electrical conductor in direct contact with the patient in an indentation on a back of the body on a left side of a spine of the body about midway between a tailbone and a waist of the body;

placing a second pad with one electrical conductor in direct contact with the patient in an indentation on the back of the body on a right side of the spine of the body about midway between the tailbone and the waist of the body;

providing an electrical connection between the first pad and the second pad by having an electrical conducting wire between the first pad and the second pad;

holding the position of the first and second pads for about two to three minutes to switch polarity back to normal for the governing meridian to allow the transfer of the internal energy flow in the body to its natural pathway.

4. A method of restoring internal energy flow of a patient along a governing meridian in the human body to a natural pathway of the body, comprising:

performing a muscle test to determine if polarity of the body is switched, the muscle test comprising:

crossing ankles of the body right over left;

placing a thumb and middle finger of a right hand together at tips of the thumb and middle finger of the right hand, so that the tips touch and the thumb and middle finger of the right hand make a circle;

taking a thumb and index finger of a left hand and positioning the thumb and index finger of the left hand so that first phalanges of the thumb and index finger of the left hand are parallel;

inserting the thumb and index finger of the left hand through the circle formed by the right hand;

mentally instructing a brain of the body to keep the thumb and finger of the right hand together for a Yes and to open for a No answer;

with the finger and thumb of the left hand inserted through the circle made by the right hand, trying to open the fingers of the left hand while questioning is the polarity of the body switched, if resistance is met from the fingers of the right hand while trying to open the fingers of the right hand, the answer is Yes, the polarity is switched, if there is a weakness in the right hand and the fingers respond by opening, the answer is No, the polarity is not switched; and restoring internal energy flow of a patient along a governing meridian in the human body to the natural pathway of the body for the polarity being switched, comprising:

placing a first pad with one electrical conductor in direct contact with the patient in an indentation on a back of the body on a left side of a spine of the body about midway between a tailbone and a waist of the body;

placing a second pad with one electrical conductor in direct contact with the patient in an indentation on the back of the body on a right side of the spine of the body about midway between the tailbone and the waist of the body;

providing an electrical connection between the first pad and the second pad by having an electrical conducting wire between the first pad and the second pad;

holding the position of the first and second pads for about two to three minutes to switch polarity back to normal for the governing meridian to allow the transfer of the internal energy flow in the body to its natural pathway.

5. A method of restoring internal energy flow of a patient along a central meridian in the human body to a natural pathway of the body, consisting of:

placing a first pad with one electrical conductor in direct contact with the patient on a front of the body about one inch above a pubic bone and on a right side of the body;

placing a second pad with one electrical conductor in direct contact with the patient on the front of the body about one inch above the pubic bone and on a left side of the body;

positioning both the first and second pads so that the first and second pads are about three inches apart;

providing an electrical connection between the first pad and the second pad by having an electrical conducting wire between the first pad and the second pad;

holding the position of the first and second pads for about two to three minutes to switch polarity back to normal for the central meridian to allow the transfer of the internal energy flow in the body to its natural pathway.

6. A method of restoring internal energy flow of a patient along a central meridian in the human body to a natural pathway of the body, comprising:

performing a muscle test to determine if polarity of the body is switched, the muscle test comprising:

crossing ankles of the body left over right;

placing a thumb and middle finger of a right hand together at tips of the thumb and middle finger of the right hand, so that the tips touch and the thumb and middle finger of the right hand make a circle;

taking a thumb and index finger of a left hand and positioning the thumb and index finger of the left hand so that first phalanges of the thumb and index finger of the left hand are parallel;

inserting the thumb and index finger of the left hand through the circle formed by the right hand;

mentally instructing a brain of the body to keep the thumb and finger of the right hand together for a Yes and to open for a No answer;

with the finger and thumb of the left hand inserted through the circle made by the right hand, trying to open the fingers of the left hand while questioning is the polarity of the body switched, if resistance is met from the fingers of the right hand while trying to open the fingers of the right hand, the answer is Yes, the polarity is switched, if there is a weakness in the right hand and the fingers respond by opening, the answer is No, the polarity is not switched; and restoring internal energy flow of a patient along a central meridian in the human body to the natural pathway of the body for the polarity being switched, comprising:

placing a first pad with one electrical conductor in direct contact with the patient on a front of the body about one inch above a pubic bone and on a right side of the body;

placing a second pad with one electrical conductor in direct contact with the patient on the front of the body about one inch above the pubic bone and on a left side of the body;

positioning both the first and second pads so that the first and second pads are about three inches apart;

providing an electrical connection between the first pad and the second pad by having an electrical conducting wire between the first pad and the second pad;

holding the position of the first and second pads for about two to three minutes to switch polarity back to normal for the central meridian to allow the transfer of the internal energy flow in the body to its natural pathway.

* * * * *